United States Patent
Toepel

(10) Patent No.: US 6,571,852 B2
(45) Date of Patent: Jun. 3, 2003

(54) COLAPSABLE, SELF-SUPPORTING, RIGID LASER CONTAINMENT BARRIER

(75) Inventor: Michael P. Toepel, Salisbury, NH (US)

(73) Assignee: Kentek Corporation, Pittsfield, NH (US)

( * ) Notice: Subject to any disclaimer, the term of this patent is extended or adjusted under 35 U.S.C. 154(b) by 0 days.

(21) Appl. No.: 09/940,559

(22) Filed: Aug. 28, 2001

(65) Prior Publication Data

US 2003/0051825 A1 Mar. 20, 2003

(51) Int. Cl.[7] ................................................. A47G 5/00
(52) U.S. Cl. .................... 160/135; 160/40; 160/229.1; 128/846; 16/268; 16/365; 250/515.1
(58) Field of Search ........................ 160/40, 135, 229.1; 128/846; 250/515.1, 516.1, 517.1; 16/268, 365, 273

(56) References Cited

U.S. PATENT DOCUMENTS

| | | | | |
|---|---|---|---|---|
| 543,906 A | * | 8/1895 | Spaulding | |
| 696,199 A | * | 3/1902 | Schmidt | |
| 1,300,722 A | * | 4/1919 | Gray | |
| 2,317,708 A | * | 4/1943 | Zareko | |
| 2,380,206 A | * | 7/1945 | Wiser | |
| 2,406,729 A | * | 8/1946 | White et al. | |
| 3,092,870 A | * | 6/1963 | Baer | |
| 3,921,225 A | * | 11/1975 | Suska | |
| 4,608,495 A | * | 8/1986 | Jacobson | |
| 4,838,525 A | | 6/1989 | Snow et al. | 256/26 |
| 5,058,863 A | | 10/1991 | Maffet | 256/26 |
| 5,199,478 A | * | 4/1993 | Kubota | |
| 5,544,436 A | * | 8/1996 | Lefkowitz | |
| 5,584,330 A | | 12/1996 | Muller | 160/135 |
| 5,992,417 A | | 11/1999 | Toepel | 128/846 |
| 6,095,226 A | * | 8/2000 | Chen et al. | |
| 6,123,321 A | | 9/2000 | Miller | 256/25 |

\* cited by examiner

Primary Examiner—Blair M. Johnson

(57) ABSTRACT

A collapsible, self-standing, rigid laser containment barrier, which includes at least two adjacent, substantially rigid laser beam absorption panels hingably attached to each other using first and second pairs of aligned hinge pins proximal top and bottom edges and near first and second sides of each laser beam absorption panel and a rigid light strip having a front face including first and second pairs of laterally extending hinge brackets. Each of the hinge bracket pairs corresponds to and is aligned with one of the first and second hinge pin pairs, and includes a hinge pin hole passing therethrough. Each of the hinge pins passes through one of the hinge pin holes to hingably attach the two adjacent laser beam absorption panels.

12 Claims, 4 Drawing Sheets

COLAPSABLE, SELF-SUPPORTING, RIGID LASER CONTAINMENT BARRIER

FIELD OF THE INVENTION

The present invention relates to a laser containment barrier and, in particular, to a collapsible, self-supporting, rigid barrier, including a rigid frame and substantially rigid, high power laser beam absorption panels affixed to the frame, a base section upon which the barrier stands, and rigid light strips, which hingably attach adjacent absorption panels.

BACKGROUND OF THE INVENTION

It is becoming more and more common to use lasers to perform industrial, medical, and research procedures. It is well-known that the radiation from such lasers must be confined to certain operative areas and that lasers used under a variety of circumstances can present a danger to personnel and equipment. It is also well-known that it is difficult to totally prevent the occurrence of stray radiation in certain circumstances.

Personnel may be injured by direct exposure to a laser beam on the skin. Also, if a person's eyes were to become accidentally exposed to a laser beam, severe injury or loss of vision can occur. Since severe or even catastrophic injuries can occur due to exposure to errant laser radiation, many laser shields have been developed.

Most laser radiation barriers or shields consist of flexible, fabric-based materials, which are used to protect personnel from scattered and diffuse laser light. These, flexible shield materials can be used to construct protective clothing and/or drapes to be worn by or placed over personnel. Flexible materials can also be used to create curtains, which may be hung from any number of support devices in order to effectively contain an area within which a laser device is to be operated. However, due to their flexibility, these laser shield materials depends upon another structure to provide support.

Recently, rigid laser containment materials have begun to be used, especially in areas exposed to high-power laser radiation or direct hits from high-power laser beams. One such laser beam absorption material is known as EVER-GUARD™, which has been sold by the Kentek Corporation of Pittsfield, N.H. the assignee of the present application for more than one year prior to the filing of the instant application. EVER-GUARD high power laser absorption panels comprise a textured surface, including a plurality of convexed dimples, which is directed toward a source of laser radiation. While EVER-GUARD panels have proven to be effective at containing high power laser radiation, they have, to date, simply been supported by existing flexible laser hanging systems, such as roller curtain tracks in areas susceptible to direct hits from high power radiation.

The Kentek Corporation has also developed a portable, self-supporting, rigid laser containment barrier, which is the subject of U.S. Pat. No. 5,992,417, the disclosure of which is incorporated herein by reference.

While the portable, self-supporting, rigid laser containment barrier offers a number of significant advantages over flexible laser blocking curtains, it would be desirable to provide a collapsable, self-supporting laser containment barrier which is made up of a plurality of substantially rigid, high power laser beam absorption, which are hingable attached to each other using a rigid light strip, which simultaneously serves as the hinged connection intermediate adjacent panels and blocks errant laser radiation intermediate the plurality of laser beam absorption panels. One or more panels may further include a base section to support the panel in a substantially vertical arrangement. Rollers or casters may also be included to facilitate the positioning and movement of the panels.

SUMMARY OF THE INVENTION

The present invention provides personnel and equipment shields which comprise a plurality of collapsible, substantially rigid, high power laser beam absorption panels. The substantially rigid panels include substantially rigid frames to which may be attached a base section upon which each panel stands. In the preferred embodiment, the rigid laser beam absorption panel is a textured material, such as EVER-GUARD laser barrier material. Furthermore, in the preferred embodiment, the collapsible, self-supporting rigid laser containment barrier disclosed herein comprises at least two adjacent rigid laser beam absorption panels. The adjacent panels are hingable attached to each other using a rigid light strip, which blocks errant radiation intermediate the adjacent panels and which allows the adjacent panels to be angularly positioned with respect to each other once they are attached.

In one preferred embodiment, each laser absorption panel includes first and second pairs of aligned and spaced hinge pins disposed at each vertical edge of each panel. One hinge pin of each pair of hinge pins is positioned near a top edge of the panel. A second hinge pin of each pair of hinge pins is positioned near a bottom edge of the panel.

Each rigid light strip includes two pairs of aligned, laterally extending brackets, each having a hole disposed therethrough, which corresponds to one hinge pin of each hinge pin pair included on each laser beam absorption panel.

Two adjacent panels are hingably attached to each other by affixing a light strip intermediate the two panels with each bracket connected to an absorption panel hinge pin. Since the pins are oriented in a vertical arrangement, the brackets are rotationally positionable with respect to each hinge pin. Thus, once assembled, a pair of panels may be rotationally positioned with respect to each other and their connecting light strip. A locking device, such as a locking pin, may be inserted through a hole in one or more hinge pin above a hinge bracket attached thereto to effectively lock the adjacent laser absorption panels together in their hingable arrangement. Of course, more than two panels may be attached in the same manner to provide large laser containment barriers.

DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
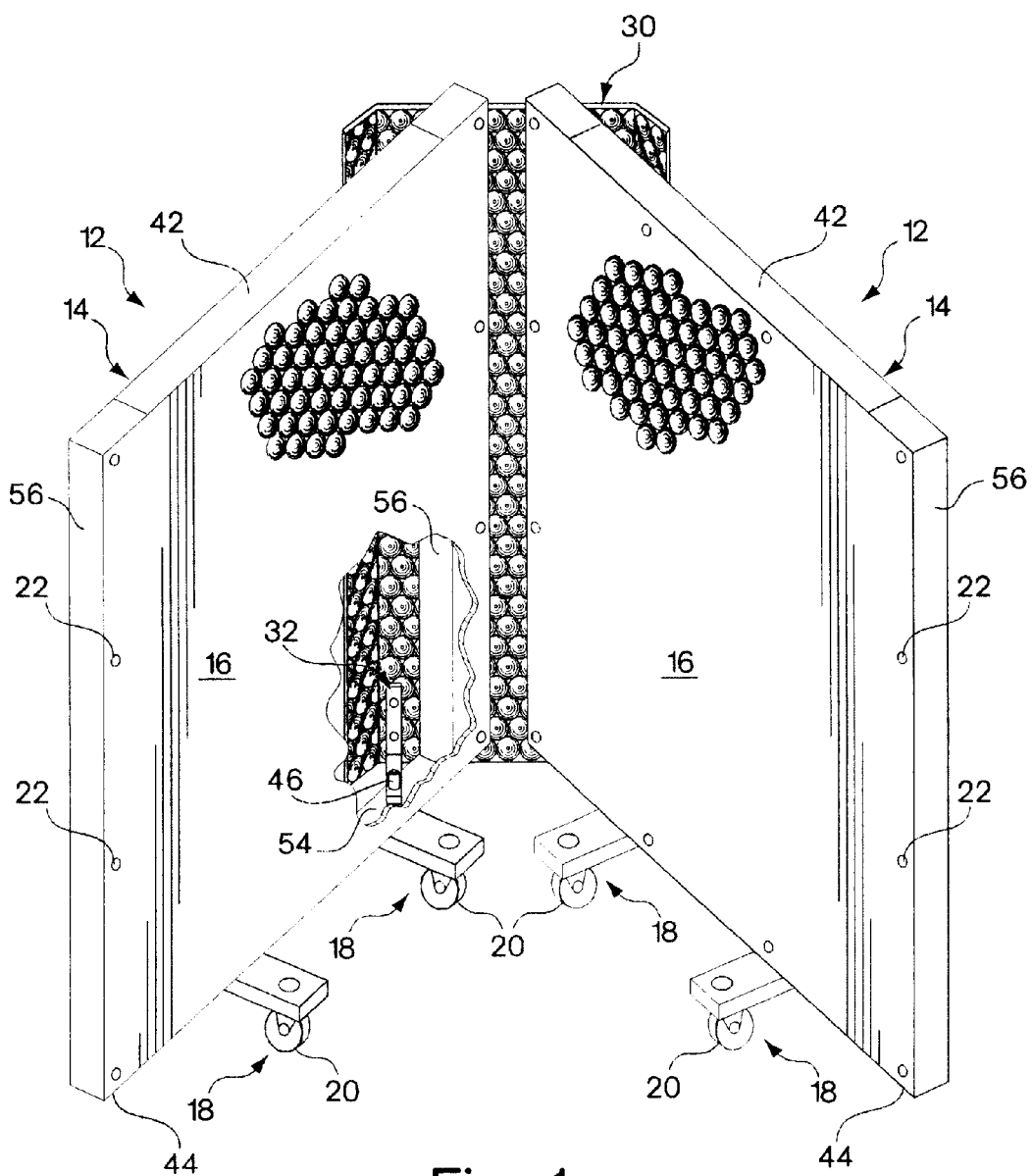
FIG. 1 is a partially cut-away, perspective view of two adjacent rigid, laser absorption panels joined by a rigid light strip and having optional base sections including casters.

Turning to the figures and, in particular, FIG. 1, a collapsible, self-supporting, laser containment barrier 10 is shown. Barrier 10 includes at least two adjacent rigid laser absorption panels 12. In one preferred embodiment, each laser absorption panel 12 includes a frame 14 having a substantially rigid laser beam absorption panel 16 affixed thereto to form a front face of each panel 12. Each frame 14 may have an optional base section 18 upon which the laser containment barrier stands. Such a base section would allow a single panel to be self-standing. Base section 18 may further include caster or rollers 20, which would facilitate the movement and positioning of a laser beam absorption panel by itself or the positioning and movement of a laser containment barrier system made up of more than one hingably attached laser beam absorption panels.

The substantially rigid, high power laser beam absorption sheet 16, which is affixed to the frame 14 of each panel 12 is preferably a metallic sheet material and, in one preferred embodiment, is made out of aluminum, due to weight considerations. The metallic laser beam absorption panel may further be textured and/or coated with a substantially black coating in order to aid in the diffusion and/or absorption of high power laser radiation.

Each laser beam absorption sheet 16 is attached to its frame 14 using a plurality of any type of suitable fasteners 22, such as screws, rivets or the like. The laser beam absorption sheet 16 may also be chemically bonded to the frame 14 or even welded thereto.

In one preferred embodiment, the substantially rigid laser beam absorption sheets 16 are EVER-GUARD sheets, which are sold by the Kentek Corporation of Pittsfield, N.H. EVER-GUARD sheets are specially designed, textured aluminum barriers which feature an absorbing, substantially black matte finish. The EVER-GUARD sheets have a front face, which includes a plurality of convex dimples. The front side of the EVER-GUARD sheet material is oriented toward a source of laser radiation. Thus, an unfocused, direct laser beam will be blocked by an EVER-GUARD sheet for extended time periods with minimal effects to the laser containment barrier.

As shown in FIG. 1, adjacent panels 12 are hingably attached to each other using a novel arrangement of hinge pins and brackets, which are included on the back side of panels 12 and on the front side of rigid light strips 30, respectively. While the following description will refer to an embodiment including two adjacent panels 12 and one intermediate, connecting light strip 30, any number of partitions may be hingably attached to each other in a like manner in order to create portable, self-supporting laser containment barriers of differing sizes and configurations. As will be more fully discussed below, the use of the combination of hinge pins 46 and 48 affixed to each panel 12 and corresponding hinge brackets 32 attached to an intermediate, rigid light strip 30 will allow adjacent panels 12 to be hingably positioned with respect to each other. Accordingly, a multi-partition barrier system will be able to be self-standing and configured and oriented to provide a simple or elaborate laser containment system.

Figure 2A:
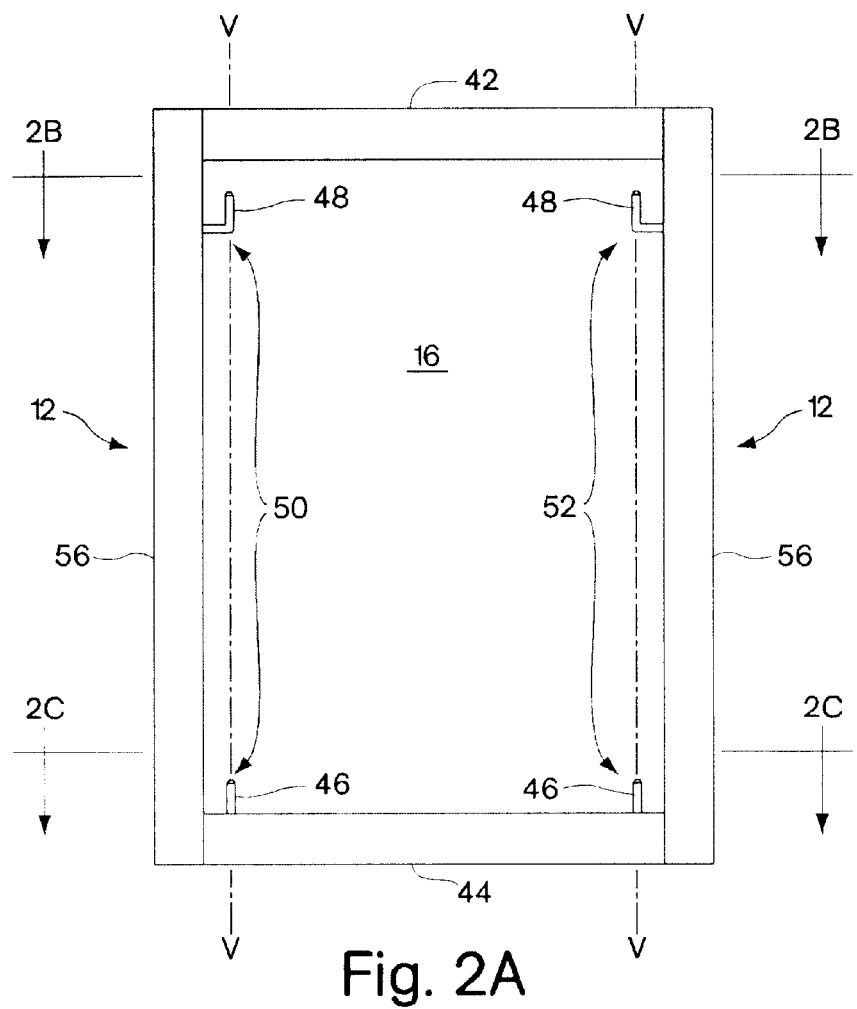
FIG. 2A is a back view of one rigid, laser absorption panel showing the two pairs of hinge pins.
Figure 2B:
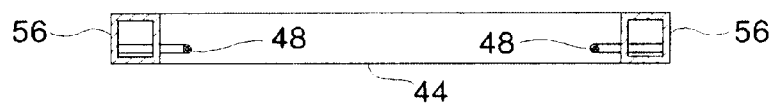
FIG. 2B is a top sectional view of the laser absorption panel of FIG. 2A taken along section BB.
Figure 2C:
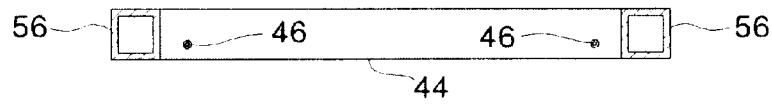
FIG. 2C is a top sectional view of the laser absorption panel of FIG. 2A taken along section CC.
Figure 3A:
FIG. 3A is a top view of a straight hinge pin of FIG. 2A.
Figure 4A:
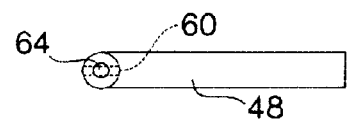
FIG. 4A is a top view of an angled hinge pin of FIG. 2A.
Figure 3B:
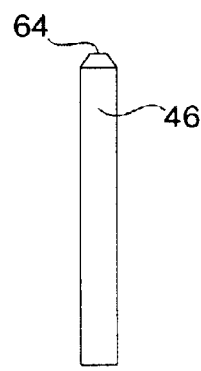
FIG. 3B is a side view of a straight hinge pin of FIG. 2A.
Figure 4B:
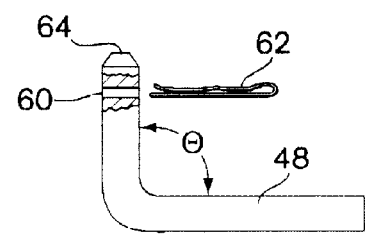
FIG. 4B is a side view of an angled hinge pin of FIG. 2A.

Turning now to FIGS. 2–4, each laser beam absorption panel 12 includes a peripheral frame 14 to which is mounted a sheet 16 of a rigid, laser beam absorption material, such as an Ever-Guard sheet. The laser beam absorption sheet 16 is mounted to a front side of each panel and extends to the peripheral edges of the frame 14. In this manner, the front side or face of each panel 12 is substantially flat, with the exception of a texture, which is preferably a convex texture, which may be provided on the front face of each sheet of laser beam absorption material affixed thereto.

On the back side of each panel 12, attached proximal a top edge 42 and a bottom edge 44 of the frame 14 are first and second pairs of aligned and spaced hinge pins 50 and 52, respectively. As is shown in FIG. 2, each of the hinge pins is aligned along a vertical axis V of each laser beam absorption panel. In this manner, the axis of rotation about the hinge pins allows adjacent panels to be rotated in a book-like fashion to vary an angle intermediate two adjacent panels. Having angles between adjacent panels allows a barrier made from a combination of a plurality of hingably attached panels to be self-standing.

In the embodiment of FIG. 2, a first hinge pin 46 of each hinge pin pair is simply a straight pin extending upwardly from a bottom member 54 of the peripheral frame 14. To facilitate the insertion of each hinge pin into a hinge bracket, each hinge pin preferably includes a chamfered top end 64. As will become more apparent below, in order to allow a light strip hinge bracket to be readily attached to each pin pair, a second hinge pin 48 of each pin pair is provided as an "l-shaped", angled hinge pin, which extends laterally from one of two panel frame side members 56, proximate the top edge of the panel 12, and then bends upwardly at and angle 9, which is preferably a 90 degree angle so that an active hinge pin portion 58 is upwardly extending and is aligned with the first hinge pin of each hinge pin pair. The hinge pins are secured to the frame side and bottom members, 56 and 54, respectively, using techniques well known to those skilled in the art of metal manufacturing, such as welding or other mechanical fastening means. More detailed views of the hinge pins 46 and 48 are shown in FIGS. 3A, 3B, 4A and 4B.

In one preferred embodiment, one or more active hinge pin portions 58 is provided with a locking hole 60, through which a locking device, such as locking pin 62, may be inserted to lock a bracket 32 onto the hinge pin 48.

Figure 5A:
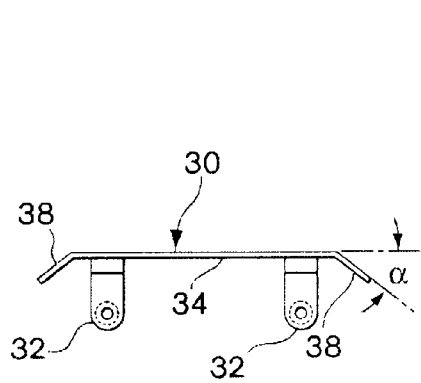
FIG. 5A is a top view of one rigid light strip with laterally extending hinge brackets to correspond to the pairs of hinge pins on adjacent laser absorption panels.
Figure 5B:
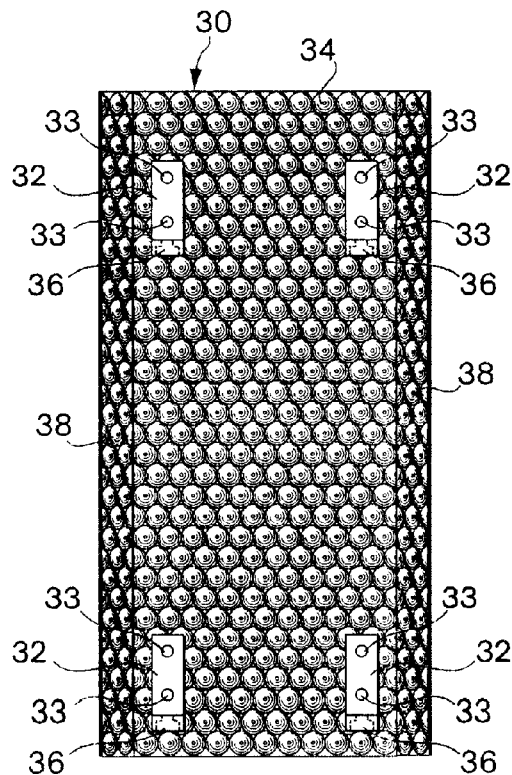
FIG. 5B is a front view of one rigid light strip with laterally extending hinge brackets.

FIGS. 5A and 5B show top and front views, respectively, of a rigid light strip 30, which hingably attaches adjacent laser beam absorption panels 12 using adjacent hinge pin pairs of the adjacent panel sections 12. Each light strip 30 is made from a rigid laser beam absorption sheet and, in the preferred embodiment is made from the same Ever-Guard sheet material that is used as the laser beam absorption sheet 16 on each laser beam absorption panel 12. Each light strip 30 has a front face 34 to which two pairs of spaced and aligned, laterally extending brackets 32 are affixed using fasteners 33. However, alternative means of fixing the brackets 32 to the light strip 30, such as welding or chemical bonding are considered equivalent. Each laterally extending bracket 32 has a hole 36 disposed therethrough, which corresponds to one of the vertically aligned hinge pins attached to adjacent laser beam absorption panels.

The front face 34 of each light strip may be the convex textured side of the Ever-Guard material to diffuse any errant laser radiation directed upon the light strip when it is used to hingably attach adjacent laser beam absorption panels 12. In one preferred embodiment, the light strip 30 includes at least one angled wing section 38, which is angled at an angle α towards the laterally extending hinge brackets 32. The angled wing section(s) 38 further assist in containing any errant radiation directed intermediate adjacent panels.

Figure 6A:
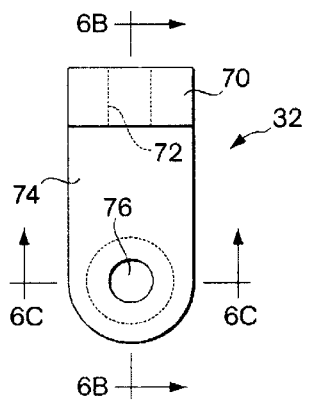
FIG. 6A is a top view of one laterally extending hinge bracket.
Figure 6B:
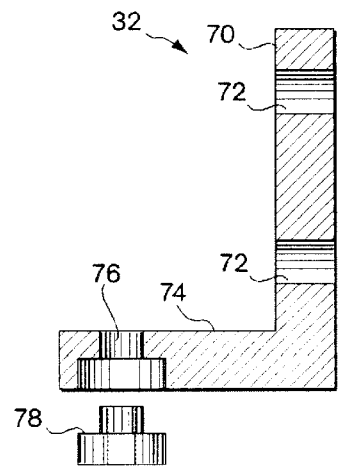
FIG. 6B is a side sectional view of the laterally extending hinge bracket of FIG. 6A, taken along section BB.
Figure 6C:
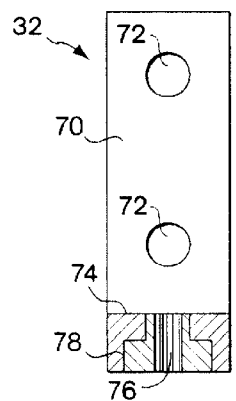
FIG. 6C is a front sectional view of the laterally extending hinge bracket of FIG. 6A, taken along section CC.

The laterally extending light strip hinge brackets 32 are shown in more detail in FIGS. 6A, 6B and 6C. Each laterally extending light strip hinge bracket 32 has a first section 70, which, when attached to a light strip, is parallel to the front face 34 of the light strip 30 to which it is attached. The first section 70 may have one or more holes 72 disposed therethrough, which, when combined with corresponding holes passing through the light strip 30 to which it is attached and suitable fasteners 33 (FIG. 5B) mechanically attach the bracket 32 to the light strip 30. Each bracket further includes a laterally extending section 74, which includes a hinge pin hole 76 through which a corresponding panel hinge pin is passed to create the hinged joint between adjacent panels. In one embodiment, the hinge pin hole 76 includes an insert 78, such as a plastic, Teflon or other friction reducing insert to facilitate the rotation of the bracket 32 about a corresponding hinge pin. Preferably, the insert 38 is replaceable and is replaced if it becomes excessively worn.

Figure 7:
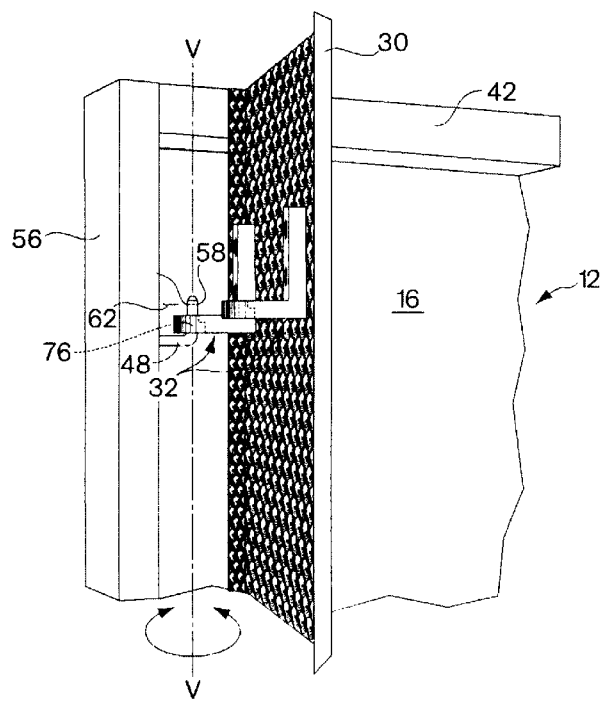
FIG. 7 is a partial perspective view of the back side of one laser absorption panel with a rigid light strip hingably attached thereto.

FIG. 7 shows a portion of the back side of one laser absorption panel 12, to which a light strip 30 is attached using bracket 32. As is shown, bracket 32, through which hole 76 passes, is inserted onto the upwardly extending, active hinge pin portion 58 of hinge pin 48. While only one hinge pin 48 is shown, one can appreciate that a light strip 30, having a total of four hinge brackets 32 is used to hingably attach adjacent laser absorption panels 12 using the two pairs of hinge pins 50 and 52 (FIG. 2A) provided on the adjacent panels 12. Locking pin 62 may be inserted through locking pin hole 30 provided in the hinge pin 48 to lock the light strip 30 onto the hinge pin 48 while still allowing the panel 12 and light strip 30 to rotate with respect to each other around vertical axis V.

As is apparent from the Drawing figures and the above described hinge elements, the beam absorption panels 14 have a substantial range of angular motion relative to each other and to the light strip 30. As illustrated in FIG. 1, the panels are movable to confront each other in a most closed position wherein their relative angular position about their hinge pin pivot axes may be relatively small, almost meeting as limited by the interference of the elements, e.g., 32 and 56. The panels may be opened relative about their respective hinge pin pivot axes to each other to be co-planar (180°), until the other, most open extreme is reached, as illustrated by FIG. 7. The most open position is limited by the width of the light strip 30, which strikes the panel element 42. Thus it is seen that the relative motion of the absorption panels is considerably greater and lesser than a co-planar disposition, and permits further contiguous connection to additional light strips and associated laser absorption panels. Furthermore, it is seen from the figures and the above description that the panels 14 sufficiently overlap the light strip 30 so as to present contiguously disposed laser absorption surfaces when viewed from the front of the laser absorption panels, which prevents the escape of laser beam containment.

Modifications and substitutions by one of ordinary skill in the art are considered to be within the scope of the present invention which is not to be limited except by the claims which follow.

What is claimed is:

1. A collapsible, self-standing, rigid laser containment barrier comprising:
    at least two adjacent, substantially rigid laser beam absorption panels, each said panel including first and second pairs of aligned hinge pins proximal top and bottom edges of each said panel near first and second sides of each said panel and having a pivot axis being disposed inwardly from the respective one of said first and second sides; and
    a rigid light strip having a front face including first and second pairs of laterally extending brackets, each said bracket pair corresponding to and having a pivot axis aligned with said corresponding one of said first and second hinge pairs, and including a hole passing therethrough and being disposed within the periphery of said front face, through which one of said hinge pins passes, wherein
        said at least two adjacent, substantially rigid laser beam absorption panels have a range of motion greater and lesser than a 180°, co-planar disposition, and
        said at least two adjacent, substantially rigid laser absorption panels and said rigid light strip form contiguously disposed laser absorption surfaces.

2. The portable, self-standing, rigid laser containment barrier as claimed in claim 1, wherein each laser beam absorption panel further includes a base section upon which each panel stands.

3. The collapsible, self-standing, rigid laser containment barrier as claimed in claim 2, wherein each base section further includes casters.

4. The collapsible, self-standing, rigid laser containment barrier as claimed in claim 1, wherein said rigid laser beam absorption material is metallic.

5. The collapsible, self-standing, rigid laser containment barrier as claimed in claim 4, wherein said metallic laser beam absorption material is coated with a substantially black matte coating.

6. The collapsible, self-standing, rigid laser containment barrier as claimed in claim 4, wherein said metallic laser beam absorption material is aluminum.

7. The collapsible, self-standing, rigid laser containment barrier as claimed in claim 1, wherein said laser beam absorption material is textured.

8. The collapsible, self-standing, rigid laser beam containment barrier as claimed in claim 7, wherein said texture includes a plurality of convex dimples on a front face of said material, said front face being oriented toward a source of laser radiation.

9. The collapsible, self-standing, rigid containment barrier as claimed in claim 1, wherein each of said at least two adjacent, substantially rigid laser beam absorption panels comprises a peripheral frame having top, bottom and side members to which said laser beam absorption material is attached.

10. The collapsible, self-standing, rigid containment barrier as claimed in claim 1, wherein said rigid light strip further comprises angled side wings.

11. The collapsible, self-standing, rigid containment barrier as claimed in claim 1, wherein said rigid light strip further comprises a friction reducing insert in each hinge pin hole provided in each laterally extending hinge bracket.

12. The collapsible, self-standing, rigid containment barrier as claimed in claim 11, wherein said insert comprises a plastic insert.

* * * * *